United States Patent [19]

Kouns

[11] Patent Number: 4,560,279
[45] Date of Patent: Dec. 24, 1985

[54] OPTICAL METHOD FOR REMOTE DETERMINATION OF THE GEOLOGICAL NATURE OF A HOMOGENEOUS SURFACE

[76] Inventor: Charles W. Kouns, 2505 Central Ave., Alexandria, Va. 22302

[21] Appl. No.: 234,748

[22] Filed: Feb. 17, 1981

Related U.S. Application Data

[63] Continuation-in-part of Ser. No. 952,059, Oct. 17, 1978, abandoned.

[51] Int. Cl.$^4$ ............................................. G01N 21/21
[52] U.S. Cl. .................................... 356/369; 356/364; 364/420
[58] Field of Search ............................... 356/364–370; 364/420, 525; 250/225

[56] References Cited

U.S. PATENT DOCUMENTS

| | | | |
|---|---|---|---|
| 3,028,596 | 4/1962 | McGillem et al. | 343/100 |
| 3,631,254 | 12/1971 | Covault | 250/225 |
| 3,700,334 | 10/1972 | Low | 356/351 |
| 3,748,484 | 7/1973 | Covault | 250/225 |
| 3,904,293 | 9/1975 | Gee | 356/369 |
| 3,992,105 | 11/1976 | White | 356/369 |
| 4,034,190 | 7/1977 | White | 235/151.3 |

OTHER PUBLICATIONS

Cacciani et al., "A Complete Stokes Meter", Solar Physics, vol. 19, 1970, pp. 270–276.
Lore, O., "Polarimetric Methods in Astrophysics", Jena Rev., vol. 15, 6–1970, pp. 330–334.
Final Report—"Experiment SO46–Visible Radiation Polarization Measurements; Phase C", NASA Doc, NAS-9-7267. Gen. Electric Co., 1–1968.
Cato, G. A., "Basic Principles of Earth Resource Sensors", pp. 64–82.

*Primary Examiner*—William H. Punter
*Attorney, Agent, or Firm*—Morgan, Finnegan, Pine, Foley & Lee

[57] ABSTRACT

An optical method for identifying an immobile target having a homogeneous surface is disclosed. Light reflected from the surface of the target is electro-optically detected. The Stokes parameters of the detected light are measured in four preselected, adjacent, spectral bands. A discrete value termed the polarization intensity index (PII) is calculated using the measured Stokes parameters. Each homogeneous surface has a characteristic PII value. Substantially identical surfaces display substantially identical PII values. By comparing PII values of unidentified target surfaces with a set of previously determined PII values for different, known target surfaces, the geological nature of an unidentified target surface may be determined.

5 Claims, 3 Drawing Figures

OPTICAL METHOD FOR REMOTE DETERMINATION OF THE GEOLOGICAL NATURE OF A HOMOGENEOUS SURFACE

This application is a continuation-in-part of my U.S. patent application Ser. No. 952,059, and filed Oct. 17, 1978 and now abandoned.

BACKGROUND OF THE INVENTION

1. Field of the Invention

This invention relates in general to the detection and analysis of reflections of a regular translational source of electro-magnetic wave radiation from preselected, unidentified, target surfaces. More particularly, the present invention relates to a method for the remote identification of a preselected, unidentified, homogeneous target surface.

2. Description of the Prior Art

It is known in the literature that the Stokes parameters of light emerging from the top of the earth's atmosphere may be predicted as a function of sun angle and viewing angle when viewing extensive areas of the earth over which the reflecting and polarizing properties are reasonably uniform. These predictions depend on detailed measurements of reflecting and polarizing properties of various materials, such as sand, clay and grass, when illuminated by sunlight. See Final Report "Experiment SO46:Visible Radiation Polarization Measurements:Phase C," NASA DOC. NAS9-7267, page 1, January, 1968. See also Oetken, "Polarimetric Methods in Astrophysics" *JENA REVIEW,* Vol. 15, page 330, June, 1970, which describes that to obtain the physical conditions of objects, the radiation from these objects is converted to Stokes parameters from which the degree of polarization (intensity), polarization directions, etc. is determined.

Moreover, there is described in an article by Cacciani and Fofi, "A Complete Stokes-Meter," *Solar Physics,* Vol. 19, pp. 270-276 (1971), apparatus for measuring Stokes parameters resulting from incident and reflected radiation. Also taught by Cacciani and Fofi is that the state of partially polarized radiation may be determined by the use of (1) azimuth determination, (2) its intensity and (3) the non-polarized background.

However, heretofore, remote sensings of target surfaces have been conducted with polarimetry on a limited basis in specialized applications. General applications to ground truth, with remote sensings of reflected light, have faltered on three technical impediments: (1) there was no imaging polarimeter in being; (2) no simple procedure existed for evaluation of the intrinsic polarization intensity of a target surface as distinguished from the optical thickness between a light source and target surface as well as from a target surface through recording; and (3) there was no discrete index to gauge the correlation of data because of the stochastic character of optical waves in thin film phenomena. Consequently, in view of the fact that polarization is a stress sensitive parameter of light, interfacial dynamics under natural conditions have tended to mask polarization signatures of target surfaces. This masking effect and the stochastic characteristics of optical waves have impeded the development of imaging polarimetry.

BRIEF SUMMARY OF THE INVENTION

Objects of the Invention

It is an object of this invention to provide a method for identifying the geological nature of a homogeneous target surface employing remote sensing means.

Another object of this invention is to provide an improved method of remote sensing of surfaces as to homogeneity and location.

An object of the present invention is to provide an improved method of remote sensing of surfaces as to horizontal or vertical orientation.

Another object is to provide an improved method of remote sensing of target surfaces as to optical thicknesses not intrinsic to the target surfaces.

Still another object is to provide an improved method of remote sensing of surfaces as to indexing stochastic averages for correlation of data.

An object of this invention is to provide an improved method of recording polarization of reflected light to determine precise correlation of measurements employing reflected sunlight.

Another object is to provide an improved method of discrimination with polarimetry to determine surface homogeneity of horizontal or vertical targets of interest ploying reflected sunlight.

These and other objects and advantages will readily become apparent to those skilled in the art in the light of the teachings hereinafter set forth.

Definitions

By "ground truth" as used throughout the specification is meant the natural discrimination between various terrain surfaces due to their intrinsic compositions such as sand, clay and rock. Such surfaces may be masked by vegetation, residuals of erosion and decomposition. Thus, in general, "ground truth" is a delineation of a natural surface of the earth. Remote sensing of target surfaces according to this invention encompasses man-made surfaces as well as spontaneous surfaces exhibited by nature. "Ground" tends to be restrictive to the planet earth whereas "surface truth" embraces the cosmos in the sense of space. Moreover, the target could be a particle, a suspension, a thin slice or surface of an inorganic or organic substance. Consequently, surfaces are referred to in this application in their broadest connotation, i.e., "surface truth".

By "stress sensitive" as used throughout the specification is meant that a target may exhibit a static equilibrium or dynamical equilibria due to its intrinsic composition be it simple and/or complex, and, as modified by any physical and chemical stresses acting thereon such as heat, loading, moisture, crystallization both internally and adjacent thereto. For example, quartz has "optical activity", i.e., the ability to rotate the plane of polarization of light. This ability may be influenced by mechanical stress and by heat which causes piezocresence or changes in the anisotrophy of crystalline material and other changes in amorphous material. If quartz is stressed beyond its elastic limit, it could have a rupture or a permanent set. With a smaller stress, the quartz could continue to have upper and lower limits of stress depending on the dynamics of its environment and its relation thereto. Also, time may be an important factor, especially in geological phenomena.

For example, if a remote sensing means of this invention is situated in a satellite which traverses in its orbit a region where quartz is unstressed, an adjacent region where the quartz is stressed and then a region where the quartz is unstressed, the spectral signatures of the two unstressed quartz occurrences might be about equal. However, the spectral signature of the strained quartz might be different because the inherent polarizing character of the stressed quartz might result in more or in less reflected and/or radiant energy reaching the scanner and being recorded when compared with the reflectants and/or radiations from the unstressed quartz. The eye or standard camera might not recognize this difference. However, the remote sensing means of the present invention as described more fully subsequently herein can discern this differentiation. Although quartz has been used as an example herein because of its abundance in nature and its diverse allotropic forms, there are many other materials existing in nature which will exhibit their intrinsic polarization signatures in both simple and complex aggregations as modified by stress.

By "look angles" as used throughout the specification are meant the orientations of the remote sensing means to intercept the reflected and/or radiated energy from a target. For horizontal targets, a vertical look angle is equal to the angle of elevation of the sun above the horizontal plane of the remote sensing means when surveyed in its operating position. It approximates the nadir angle of the sun to the elevation of the remote sensing means. However, since the angle of reflection on a target is equal to the angle of incidence from the light source, the remote sensing means is depressed by this angle below the horizontal plane of the remote sensing means to intercept the reflected energy. The horizontal look angle is equal to the angle of azimuth of the sun measured from true north clockwise to the remote sensing means—sun line of sight at the remote sensing means. For vertical targets, the "look angles" are different as indicated subsequently herein.

By "optical waves" as used throughout the specification is meant those waves reflected and/or radiated by the full range of the electromagnetic spectrum.

By "remote sensing" is meant the science and art of acquiring information about material things from measurements made at some distance without direct physical contact of those things.

By "radiation" is meant the emission and propagation of energy through space or through a material medium in the form of waves.

BRIEF DESCRIPTION OF THE INVENTION

It has now been found that a relatively simple and effective optical method is provided for remote identification of the geological nature of homogeneous target surfaces. The nature of a target surface composition, such as part of the earth's terrain, can be remotely sensed, analyzed and identified geologically according to the present invention. The surface may be either stationary or moving relative to the remote sensing system.

A remote sensing means, preferably consisting of a polarimeter, is employed to sense reflections of a regular translational source of electromagnetic wave radiation, such as the sun, from the surface of the target to be geologically identified. The remote sensing means should be stationary with respect to the target at time when readings are taken to avoid spurious data being collected. In one embodiment of the present invention, the remote sensing means is mounted to a transit base rigidly positioned above the earth and within its atmosphere. In another embodiment, the remote sensing means is mounted to a transit base which base is rigidly positioned exterior of the earth's atmosphere, such as in an orbiting satellite.

In either of the two embodiments discussed hereinabove, the remote sensing means is aimed directly at the sun and elevation and azimuth are sensed and recorded. The remote sensing means is then aimed at the ground at the same azimuth and at a depression angle equivalent to the formerly recorded elevation angle. The target is then defined by the area around the line intercepting the ground. The objective is to have the remote sensing means receive reflected light directly from the sun.

According to the present invention, it has been found that a target area between about $\frac{1}{2}$ foot and about 2 feet in diameter may be identified as to its geological nature by use of the remote sensing means. When substantially horizontal targets are desired to be identified, it has been found that there should be about 40 meters in distance between the remote sensing means and the target per 2 meters in diameter of the horizontal target. This rule of thumb applies to the embodiment of applicant's invention wherein the remote sensing means is fixedly mounted to a base situated within the earth's atmosphere. In the embodiment of applicant's invention wherein the remote sensing means is mounted to a base situated exteriorly of the earth's atmosphere, it is believed that there should be about 20 kilometers in distance between the remote sensing means and the target per 1,000 meters in diameter of the horizontal target.

As indicated previously herein, the remote sensing means with a nadir orientation intersecting a truly horizontal surface would cover a circle of 1 foot diameter for each 20 feet of elevation above the horizontal surface. This ratio and other ratios previously described herein can be modified, if desired, by engineering design of the remote sensing means to the resolution desired. The resolution can thus be adjusted by proper selection of the wavelengths of energy being sensed. In the visible region, the wavelengths are on the order of 0.001 cm, while in the microwave region, the wavelengths are on the order of whole centimeters.

When a substantially horizontal surface is targeted using a polarimeter as the remote sensing means, the target is typically quasi-circularly shaped. When a substantially vertical surface is targeted using a polarimeter as the remote sensing means, the target is circular in shape.

The remote sensing means is designed to filter received light into four preselected wavelengths $\lambda n$ through $\lambda n+3$, and read out the Stokes Parameters Q,U and I for each of the preselected wavelengths, from which a polarization intensity (PI) for each preselected wavelength can be derived. For targets comprised of a homogeneous surface, it has been found empirically that conjugate bands ($\lambda n$ and $\lambda n+1$) in a given spectrum will have the same value of PI as will be the case with the conjugate bands ($\lambda n+2$ and $\lambda n+3$) in a different spectrum. It has also been discovered that the PI values for $\lambda n$ and $\lambda n+1$ will be different than the PI values for $\lambda n+2$ and $\lambda n+3$ and the relationship of that difference will vary from material to material.

Moreover, it has also been discovered that if the target is not homogeneous, the PI values for all four preselected wavelengths, $\lambda n$ through $\lambda n+3$ will vary. The relationship of the difference in PI values between conjugate bands in two spectra defines a polarization intensity index (PII) which, in effect, is a characteristic signature of a homogeneous surface. By comparing and correlating known PII values with measured PII values of unidentified target surfaces according to this invention, it is possible to identify the geological nature of a homogeneous target surface via remote sensing means.

The features that characterize the novelty of the present invention are set forth with particularity in the appended claims. Both the organization and manner of operation of the present invention, as well as other objects and advantages thereof, will be apparent by reference to the detailed description which follows taken in conjunction with the accompanying drawings wherein like reference symbols designate like parts throughout the figures thereof.

DESCRIPTION OF THE PREFERRED EMBODIMENTS

Figure 1:
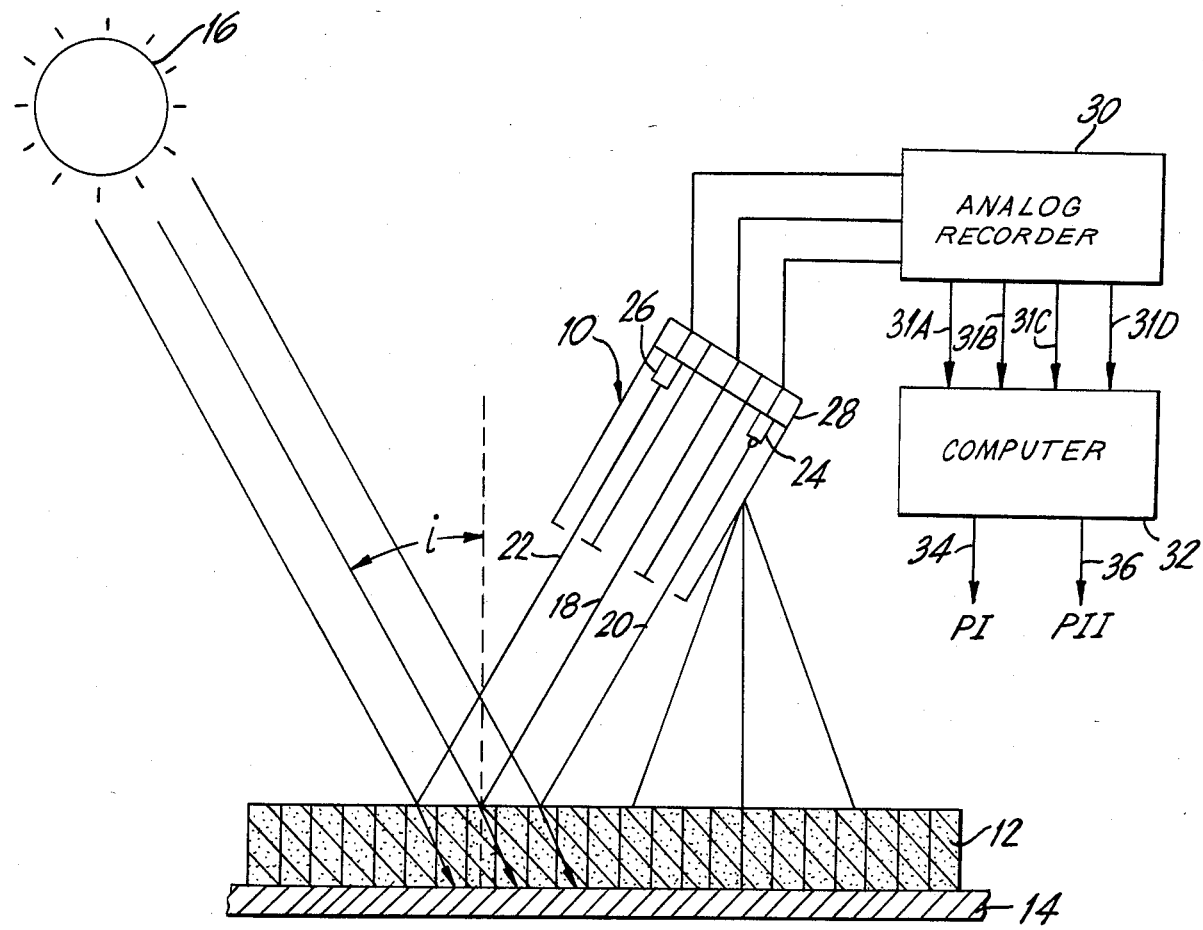
FIG. 1 is a schematic diagram of an embodiment of a polarimeter apparatus for carrying out the present invention for substantially horizontal targets.

As understanding of the underlying concepts associated with the present invention is necessary to an appreciation of the function of the remote sensing means of the present invention, the following discussion includes references to well-understood principles of optics which form part of the basic foundation of applicant's invention.

Based upon empirical measurements in the laboratory, applicant has found that fixed illumination of a target surface (passively as by a rigidly oriented lamp or actively as by a sun-synchronous orbiting satellite platform) has the practical effect of simulating a single optical plate which exhibits thin film characteristics of reflection and refraction by Fresnel's Laws. Under these conditions, polarization intensities of homogeneous target surfaces are distinctive for adjacent spectral bands in the system as if each band were independent of the other bands.

Based upon further empirical measurements outside of the laboratory (in the field), applicant has further found that regular translational illumination of a target surface (passively as by the sun or actively as by controlled artificial light) has the practical effect of slicing the target surface into a statistical array of parallel-adjacent optical plates each of which exhibits thin film characteristics of reflection and refraction by Fresnel's Laws. Under these conditions, polarization intensities of homogeneous target surfaces are equal for conjugate pairs of adjacent spectral bands in the system. The conjugate pair grouping is different for substantially horizontal target surfaces and for substantially vertical target surfaces. Also, the magnitudes of polarization intensities differ for different pairs of spectral bands in the system.

In brief, applicant has discovered that the polarization intensities of substantially homogeneous target surfaces are constant when they display the same thin film characteristics of reflection and refraction by Fresnel's Laws under identical conditions. Interference spectroscopy of a target surface, studied with regular translational illumination, will yield results dependent on the translational speed of the illumination providing all other pertinent factors remain unchanged. Thus, within the limits of instrument precision, a generally horizontal target surface which is optically homogeneous, in terms of thin film characteristics of reflection and refraction, will exhibit virtually the same polarization intensities under solar lighting in different states of the United States or in different countries of the world providing other pertinent factors remain unchanged. These pertinent factors include target latitude. The same logic applies equally to a generally vertical target surface and to target surfaces oriented between the two extremes of vertical and horizontal.

Thus, applicant's invention is based upon the discovery that optically homogeneous target surfaces have distinctive interference signatures for their orientations as well as for their substance. In other words, all surfaces may be identified as to their substance and orientation whenever regular translational illumination passes over them and is reflected back as modified by the thin film characteristics of all the boundaries involved. The complexities of evaluating all the boundaries involved may be appreciated from a consideration of the well-known complexities involved in the performances of thin-film optical devices from a qualitative viewpoint since according to applicant's invention, target surface behavior analogs that of thin-film optical devices. For example, H. A. McLeod in "Thin Film Optical Filters", American Elsevier Publishing Company, Inc., New York, 1969, at page 4 lists several factors involved in understanding in a qualitative way the performance of thin-film optical devices as follows: (1) The amplitude reflectance of light at any boundary between two media is given by $(1-p)/(1+p)$, where p is the ratio of the refractive indices at the boundary (the intensity reflectance is the square of this quantity; (2) There is a phase shift of 180° when the reflectance takes place in a medium of lower refractive index than the adjoining medium and zero if the medium has a higher index than the one adjoining it; (3) If light is split into two components of reflection at the top and bottom surfaces of a thin film, then the beams will recombine in such a way that the resultant amplitude will be the difference of the amplitudes of the two components if the relative phase shift is 180°, or the sum of the amplitudes if the relative phase shift is either zero or a multiple of 360°. In the former case, the beams are said to interfere destructively and in the latter case constructively. Other cases where the phase shift is different will be intermediate between these two possibilities.

A review of optical principles dealing with interference is found in Drude, P., "The Theory of Optics" (Translated from the German by C. Riborg Mann and Robert A. Millikan), Dover Publications, Inc., NY, 1959, pages 130-134, incorporated herein by reference. The optical train of the remote sensing means, the photo-polarimeter, of applicant's invention can be compared with the optical train of the Fresnel Mirror Experiment set forth in Drude, supra to rationalize the interference spectroscopy. However, Fresnel's experiments did not relate to regular translational illumination.

In thin-film optics, the trace of a beam of light that is refracted may form a symmetrical Vee (a reflected ray that is refracted) in an isotropic target. With an array of such parallel beams, the walls of such Vees or echelletes constitute a pair of adjacent "mirrors". The wedge of solid material outlined by such "mirrors" constitutes a wedge. At the surface of such an isotropic target, fixed illumination will produce an array of Vees below the isotropic surface and wedge bases or echelles at the isotropic surface in response to wave lengths of the illumination and their orientation.

Regular translational illumination will produce an array of Vees below the isotropic surface of a target in addition to producing a light and shadow diffraction grating at the surface of overlapping wedge-bases activated by the modulation effects of the translational illumination. Reflected rays from these events will escape refraction, but they may still combine constructively or destructively with refracted rays in parallel orientation. Applicant has discovered that these combined refracted-diffracted phenomena may be telemetered as conjugate pairs of signatures for homogeneous surfaces and their general horizontal and vertical orientation.

While not wishing to be bound by any theory of the invention, it is believed that the conjugate pair phenomena discovered by applicant indicate that radiant energy vibrates in regular harmonic waves in homogeneous systems. Also, the conjugate pair phenomena are dependent on the paths through which trains of energy move at a constant rate of speed in diffraction and in refraction modes, respectively.

Splitting radiant energy in a polarimeter renders the process of telemetry also one of interferometry only if modulation of the radiant energy is produced. Without modulation of the radiant energy under telemetry, the target behaves as a single optical plate such that filtration of each wave length yields a different value. The conjugate pairing phenomena of applicant's invention would not occur.

According to applicant's invention, however, modulation of radiant energy is produced by the ephemerides of an energy source (regular translational motion) be it incidance or exitance as emitted, reflected or transmitted. Modulation patterns in natural systems create statical arrays of echelletes (which analog troughs of ocean waves) and echelles (which analog crests of ocean waves).

In optical phenomena, such troughs are the paths of beams governed by Fresnel's Laws of refraction and reflection. The crests are the entrance and exit traces of those beams at the target surface. Troughs are governed by chromatic refractions; crests are governed by achromatic diffractions. Any optical signature of the target then is governed by Fresnel's Laws of refraction and reflection, and by Vasco Ronchi's interferometry of optical systems with diffraction gratings. The combination of interferential effects of the optical refraction and reflection phenomena of a target interacts with the interferential effects of the optical diffraction phenomena of the target to produce an optical signature of the target. Applicant's autocorrelation telemetry samples these signatures through time, by chromatic wave lengths which analog sampling of radiant flux density by successive monochromatic sources in turn.

Conjugate pairs of spectra represent symmetry of ordinates in harmonic curves of wave propagation of the optical system (as may be observed in sine waves). With wave crests and troughs from 0° to 360°, each pair of conjugate ordinates will have a positive and a negative pair. Dissymmetries of ordinates will be revealed as inhomogeneities due to optical interference effects of the target that disrupt pure harmonic symmetry. In this connection, inhomogeneities that correlate would be similar. Symmetries of ordinates, as in undistorted harmonic curves, will reveal homogeneity of a target surface. In addition, the grouping of the conjugate pairs of polarization intensities by wave length will reveal if the target is generally horizontal or generally vertical.

Echelletes produce the same kinds of effects that Fresnel's Mirror experiment produced with constructive or destructive interference of energy trains. Consequently, not only can a photopolarimeter be used to measure such phenomena (as described herein) but an interferometer such as an optical wedge (Lenouvel's Wedge) or Fresnel's Mirrors may be employed. Echelles produce the same kinds of effects that Vasco Ronchi's Diffraction Gratings produce in optical systems with diffraction interference images.

Applicant's remote sensing system thus provides for analog telemetry of chromatic refractive phenomena of targets of interest irradiated by electromagnetic fluxes. The statistical array of Vees or eschelletes of incidance on the targets and exitance from the targets synthesize diffraction grills between the target and its reflected beams. Achromatic diffraction phenomena of these synthesized grills or eschelles produce constructive and destructive interferences between incidance and exitance fluxes on targets. A natural or empirical light source, of spectra comprising sunlight, that modulates the light beams of the system, by regular translational motion, creates a synchronous system and causes the targets to behave as interferometers. Autocorrelation of these systems by analog telemetry prints out signature reflections which are converted mathematically to polarization intensities for discrete spectra used as filters synchronously and sequentially. In turn, these polarization intensities are converted mathematically to polarization intensity indices to facilitate correlations of data by single parameters.

With regular non-translational illumination, polarization intensity measurements of various targets have been influenced by six factors: the elevation and azimuth angles of the illumination source of the target and the photo-polarimeter thereon; the spectral wave lengths employed in the measurements; and, the condition of the target surface being measured. Also, it is known that each wave band displays its own polarization intensity for each target as if it were alone.

However, according to applicant's method, the number of variables for any one target have been reduced. Two polarization prisms situated in the remote sensing means of applicant's invention are set at 90° and 180°, respectively, from the vertical in a common plane. Thus, when the remote sensing means is employed for surveying, the polarizing prisms therein are identically oriented for each target. Moreover, the elevation and azimuth of the look angle on the target are oriented to the elevation and azimuth angle of the sun illumination to maximize the target flux in the common vertical plane intersecting the sun, the target and the remote sensing means. Four spectral wave bands have been found to be stable in bandpass values and in constant speed of rotation parallel to the plane containing the stable polarizing prisms. The wave bands for reflectants are $\lambda_n = 0.5-0.6\mu m$; $\lambda_{n+1} = 0.6-0.7\mu m$; $\lambda_{n+2} = 0.7-0.8\mu m$; and $\lambda_{n+3} = 0.8-1.1\mu m$. The look angles are constant for any one target. The illumination angles may vary slightly due to the motion of the sun during the time (in seconds) of data sensing and recording on any one target. The generally horizontal or vertical target surface conditions of ground truth may be assumed as constant for the recording time employed, generally in the order of seconds.

For wave lengths in the emissive region of the electromagnetic spectrum, emissions from the targets may be telemetered in lieu of reflectants from the targets. The selection of telemetry wave bands then would be governed by well known mathematical operations such as by the Theorem of Mean Value.

One set of readings takes about 1.3 seconds. In 6 seconds, 4 complete readings can be taken and recorded. If the remote sensing means were aboard a satellite hovering in space at the time of recording, it would still take about 1.3 seconds to complete one reading. This is due to the magnitude of difference between the speed of the sunlight and the speed of the earth, i.e., 186,000 miles per second to about 1,000 miles per hour viz-a-viz the sun at the Equator. The speed of the earth decreases gradually to zero at the respective Poles.

The differential variability of the sun-source illumination for a brief period of time, generally in the order of seconds and preferably up to about six seconds, by translational motion substantially satisfies Fresnel's-mirrors experiment for $\lambda n$ and $\lambda n+1$ as a conjugate pair and for $\lambda n+2$ and $\lambda n+3$ as a conjugate pair with near horizontal targets that are homogeneous at their surfaces. It is thus believed that statistical limits of destructive and constructive interference are induced by interaction of the mobile sun source flux on the polarizing prisms as conditioned by ground truth of the target for adjacent wave bands because the regular translational motion of the light source has the practical effect of "slicing" the target surface into an array of parallel and adjacent plates. It is also believed that the flux from each plate includes rays from surface reflections plus waves from refracted reflections. The target media and their optical character determine what portion of the refracted beams emerge at the target surface and travel parallel to the surface reflections that escaped refraction. This "stream" of parallel reflections is essentially an optical signature input into the remote sensing means of applicant's invention. The remote sensing means discriminates the optical signature input in terms of its polarization intensities ($PI_s$) by means of the Fresnel-mirrors analogy.

Each homogeneous target which is substantially horizontal has associated therewith, under similar conditions, a polarization intensity index (PII) signature according to the formula:

$$PII_H = \frac{(PI\lambda n + PI\lambda n + 1) - (PI\lambda n + 2 + PI\lambda n + 3)}{(PI\lambda n + PI\lambda n + 1) + (PI\lambda n + 2 + PI\lambda n + 3)}$$

It is noted that ($PI\lambda n + PI\lambda n + 1$) indicates that the spectra $\lambda n$ and $\lambda n+1$ were observed to display equal polarization intensities as a conjugate pair. The same is true for the spectra $\lambda n+2$ and $\lambda n+3$. Minor differences in the index signatures for identical horizontal surfaces relate to breaks or masking of the homogeneity.

A similar rationalization applies for field targets which are substantially vertical. In such case, the conjugate pairs are $\lambda n$ with $\lambda n+3$ and $\lambda n+1$ with $\lambda n+2$. Each homogeneous target which is substantially vertical has associated therewith, under similar conditions, a PII signature according to the formula:

$$PII_v = \frac{(PI\lambda n + PI\lambda n + 3) - (PI\lambda n + 1 + PI\lambda n + 2)}{(PI\lambda n + PI\lambda n + 3) + (PI\lambda n + 1 + PI\lambda n + 2)}$$

The autocorrelation of conjugate pairs of wave bands, since it renders all stress history in the system common to the height of the remote sensing means above a target, allows for surface correlations by comparisons despite the elevation of the instrument above the target surface. Utilizing the method of applicant's invention, land surfaces may be accurately mapped with precise registration for their instrinsic composition and orientation, including vertical surfaces of canyons, wells and mines. Subtle differences in ground truth associated with surface halos indicative of fossil fuels and other important minerals may also be identified. Moreover, by employing polarimetry in the range of Angstrom units ($10^{-8}$ cm), reflected light studies of natural and empirical microscopic specimens may be made according to applicant's invention. Other applications of applicant's method include the identification of crops and range land. Because changes in elevation of the remote sensing means of applicant's invention in the same region of latitude do not impact the conjugate pair phenomena, applicant's method, with its integration of variables in data results of the polarization intensity, provides a comparative calculus for deep space research by empirical methods with resolution of surface areas adjusted by the selection of instrument-target distances.

When the remote sensing means is mounted within an orbiting satellite, it is preferred that the orbit be sun synchronous to avoid the Doppler effect for either a near horizontal target or a near vertical target. Such a system negates the natural and regular translational illumination in the system of applicant's invention. At the time of recording, a hovering satellite would be suitable for sensing of near horizontal or near vertical surfaces. However, the remote sensing means if situated aboard an orbiting satellite, would need to incorporate transit characteristics for "look angles" and precision. For near horizontal targets in applicant's method of remote sensing, the rotation of the earth counter-clockwise on its axis in the Northern Hemisphere (clockwise in the Southern Hemisphere) has the effect of algebraically decreasing the speed of light impacting the target in the Northern Hemisphere (algebraically increasing the speed of light impacting the target in the Southern Hemisphere.) For near vertical targets in applicant's method of remote sensing, the revolution of the earth counter-clockwise in its ecliptic about the sun in the Northern Hemisphere (clockwise in the Southern Hemisphere) has the effect of algebraically decreasing the speed of light impacting the target in the Northern Hemisphere (algebraically increasing the speed of light impacting the target in the Southern Hemisphere). In each instance, the Doppler Effect is intrinsically corrected for by causing the adjacent filter bands in the optical system to indicate equal amplitudes of reflected Irradiation Flux and/or radiated energy whenever the target is homogeneous. This is in accord with Fresnel's Laws for thin films. If the target is not homogeneous in accordance with Fresnel's Laws, the adjacent filter bands in the optical system indicate unequal amplitudes of reflected Irradiation Flux and/or radiated energy.

Referring to FIG. 1, there is shown one embodiment of an apparatus for carrying out applicant's invention. The apparatus consists of a polarimeter 10 for geological remote sensing, i.e., the determination of the nature of a near horizontal earth surface composition by remote sensing means. The polarimeter device is known as the "Visible Light Polarimeter-Lab. Type SO46"

(commercially available from General Electric Company, Space Division, P.0. Box 8555, Philadelphia, Pa. 19101). The SO46 Type Photopolarimeter is a scientific device intended to be used for the measurement of the Stokes parameters of a light flux in each of several wavelength intervals of light. The values of the Stokes parameters may be used to calculate the degree of polarization of the light flux. A more detailed description of the instrument is reported at the Ninth International Symposium on Remote Sensing of Environment, April, 1974 or in "Visible Light Photopolarimeter System for Field Studies", General Electric Company, Space Division, Space Sciences Laboratory King of Prussia, Pa., Jan. 5, 1977.

Light is received and transmitted through the polarimeter to a light detector in each of three optical paths. Electrical signals generally internally in response to this light are called B, D and $\frac{1}{2}$I. They are related to two of the Stokes parameters, Q and U, as follows:

$$\tfrac{1}{2}Q = B - \tfrac{1}{2}I \text{ and}$$

$$\tfrac{1}{2}U = D - \tfrac{1}{2}I$$

This subtraction is performed within the photopolarimeter 10 and the output of the instrument is a continuous series of pulses in which the values of Q, U and I in one wavelength band, are given by the magnitude of three consecutive pulses, then the values of Q, U and I, for another band, are given etc. for each of the wavelength bands and then the sequence returns to the first band again. The Stokes parameters Q, U and I are related by the following equations:

I = total intensity of light

Q = IP cos (2×)

U = IP sin (2×)

P is the degree of polarization of the reflected light flux; I is the total intensity of light; and x is the angle the plane of polarization makes with the vertical.

Since $\cos^2 A + \sin^2 A = 1$, P may be calculated by the following equation:

$$P = \sqrt{\frac{Q^2 + U^2}{I^2}}$$

The filter bandwidths employed according to applicant's invention are as follows:
0.5 to 0.6 micrometer
0.6 to 0.7 micrometer
0.7 to 0.8 micrometer
0.8 to 1.1 micrometer In the GE presentation of the Stokes Parameters for the SO46 instrument, "P" is used as a factor to indicate the degree of polarization or the polarization intensity of the reflected light flux. It is felt that using Polarization Intensity (PI) is a more suitable acronym than (P) since it connotes both first letters of a two-word factor.

This acronym in no way should be confused with the algebraic product used by GE in which P stands for degree of polarization of the reflected light flux, and, I stands for the total intensity of light:

$$\text{Applicant's } (PI)_{\lambda n} = \text{GE's } (P)_{\lambda n} = \sqrt{\frac{Q^2_{\lambda n} + U^2_{\lambda n}}{I^2_{\lambda n}}}$$

Referring now to FIG. 1, there is shown a layer of sulfur 12 whose mean thickness and electrical properties, in addition to the electrical properties of a soil substrate 14 resting beneath it, are unknown. Natural radiation from sun 16 is intercepted at the sulfur layer 12. Reflected energy from the top surface of the sulfur layer 12 is sensed by optical channels 18, 20, and 22 of the polarimeter 10 on a transit base and directed in amplitude detectors 24, 26 and in wavelength detectors 28 the output of the wavelength detectors 28 is fed to an analog recorder 30. The information received from the analog recorder 30 is analyzed in a computer 32 to derive the polarization intensities of the filtered spectra according to the formula mentioned previously herein. The outputs of the computer 32 corresponding to the computed PI and PII are designated by the numerals 34 and 36, respectively.

Analog recorder 30 and programmable computer 32 are well-known commercial items and will not be described in detail since they are not essential to the method of applicant's invention.

The SO46 photopolarimeter 10 contains three optical channels 18, 20 and 22. The channels 20 and 22 contain Glan Thompson type polarizing prisms in the focal region of the collimating lenses. Measurement of the Stokes Parameters: $\frac{1}{2}$I on channel 18, Q on channel 20 and U on channel 22 are made by comparing the orthogonal polarized beams 24 and 26 with the beam 18. Comparison of the beams is effected by an electromechanically driven beam selector wheel (not shown) which is placed in the focal plane of the three collimating lenses. The Glan Thompson type prisms are oriented to accept light polarized at angles of 90° (beam 24) and 180° (beam 26) from the vertical. These polarized components are designated B and D, respectively. The parameters Q and U are obtained as the differences I−2B and I−2D. Between the two channels 20 and 22 with the prisms in the same common plane (perpendicular to the longitudinal axes of the channels) are windows which pass light flux being reflected by the target surface. The channel 18 is labeled $\frac{1}{2}$ (I).

To the rear of the fixed B-D-I plane 20, 22 and 18, there is fitted a parallel rotating plane 28 with four spectral filters on a common arc in the order $\lambda n+2 = 0.7-0.8$ micrometers; $\lambda n+1 = 0.6-0.7$ micrometers; $\lambda n = 0.5-0.6$ micrometers; and $\lambda n+3 = 0.8-1.1$ micrometers. These filters pass the vertical and the horizontal components in quadrature of polarized reflectance from the target surface simultaneously for their respective wave bands 28 concurrently with the free flowing light flux 18 reflected from the target. The timing is geared to a Geneva movement so that one complete pulse of all four bands 28 is cycled in 1.3 seconds. This provides a coded print-out Q, U and $\frac{1}{2}$(I) for each of the four spectral bands 28. These terms are known as Stokes parameters for polarized light. They are converted to a polarization intensity 34 expressed as a ratio by solving the equations for each wave band, respectively, according to the formulae:

$$100 \, PI_{\lambda n} = 100 \sqrt{\frac{Q^2_{\lambda n} + U^2_{\lambda n}}{I^2_{\lambda n}}}$$

$$100 \, PI_{\lambda n+1} = 100 \sqrt{\frac{Q^2_{\lambda n+1} + U^2_{\lambda n+1}}{I^2_{\lambda n+1}}}$$

$$100 \, PI_{\lambda n+2} = 100 \sqrt{\frac{Q^2_{n+2} + U^2_{n+2}}{I^2_{n+2}}}$$

$$100 \, PI_{\lambda n+3} = 100 \sqrt{\frac{Q^2_{n+3} + U^2_{n+3}}{I^2_{n+3}}}$$

The polarimeter 10 is preferably fitted to a biaxial yoke (not shown) with a transit style mounting to facilitate precise orientation and registration of traverses by latitude and longitude. In addition, the case (not shown) of the polarimeter 10 is fitted with a gun sight telescope and sun shield for manual tracking of the sun and other targets. The polarimeter 10 is linked by a cable (not shown) to a central control panel (not) shown) and electronics package (not shown) powered by a portable 12 V storage battery unit with an AC inverter and a constant voltage source. The control panel is linked by a cable to a recorder 30 that prints out Q, U and ½ I values cyclically in 12 coded line pulses by band sequence 0.7-0.8 micrometers on line 31A ($\lambda n+2$); 0.6-0.7 micrometers on line 31B ($\lambda n+1$); 0.5-0.6 micrometers on line 31C ($\lambda n$); and 0.8-1.1 micrometers on line 31D ($\lambda n+3$).

In operation, the polarimeter 10, mounted on a rigidly positioned transit base, is aimed directly at the sun and elevation and azimuth angles are recorded. The polarimeter 10 is then aimed at the ground at the same azimuth angle and at a depression angle equivalent to the formerly recorded elevation angle. The target is then defined by the area around the line intercepting the ground. The objective is to have the polarimeter receive reflected light directly from the sun.

The polarimeter 10 filters received light in four wavelengths $\lambda n$ through $\lambda n+3$, and the recorder 30 reads out the Stokes parameters Q, U and ½ I for each of the wavelengths $\lambda n$ through $\lambda n+3$, respectively, on lines 31A to lines 31D, respectively. Polarization intensity (PI) for each wavelength, $\lambda n$ through $\lambda n+3$ respectively, as well as a polarization intensity index (PII) for the target, can then be derived in computer 32 as discussed previously herein.

PI$\lambda n$ indicates the polarization intensity calculated for a surface target in a traverse for spectra $\lambda n$. PI$\lambda n+1$ indicates the polarization intensity calculated for the same surface target in a traverse for spectra $\lambda n+1$. PI$\lambda n+2$ indicates the polarization intensity calculated for the same surface target in a traverse for spectra $\lambda n+2$. PI$\lambda n+3$ indicates the polarization intensity calculated for the same surface target in a traverse for spectra $\lambda n+3$.

If PI$\lambda n+2$=PI$\lambda n+3$; and, if PI$\lambda n$=PI$\lambda n+1$, the same target in a traverse is observed to display equal polarization intensities by conjugate pairs of spectra. If these conjugate pairs of spectra also display unequal magnitudes of polarization intensities respectively in which PI$\lambda n$/PI$\lambda n+1$ is greater than PI$\lambda n+2$/PI$\lambda n+3$, such targets are near horizontal in orientation and they are homogeneous in substance. If the target is not homogeneous, PI$\lambda n$ through PI$\lambda n+3$ values of polarization intensities will all vary with respect to one another. For correlation of such horizontal targets with similar horizontal targets, the Polarization Intensity Polarization Intensity Index of Horizontal Targets ($PII_H$) =

$$\frac{(PI\lambda n + PI\lambda n + 1) - (PI\lambda n + 2 + PI\lambda n + 3)}{(PI\lambda n + PI\lambda n + 1) + (PI\lambda n + 2 + pI\lambda n + 3)}$$

If the target is not homogeneous, PI$\lambda n$ through PI$\lambda n+3$ values of polorization intensities will all vary with respect to one another.

Figure 2:
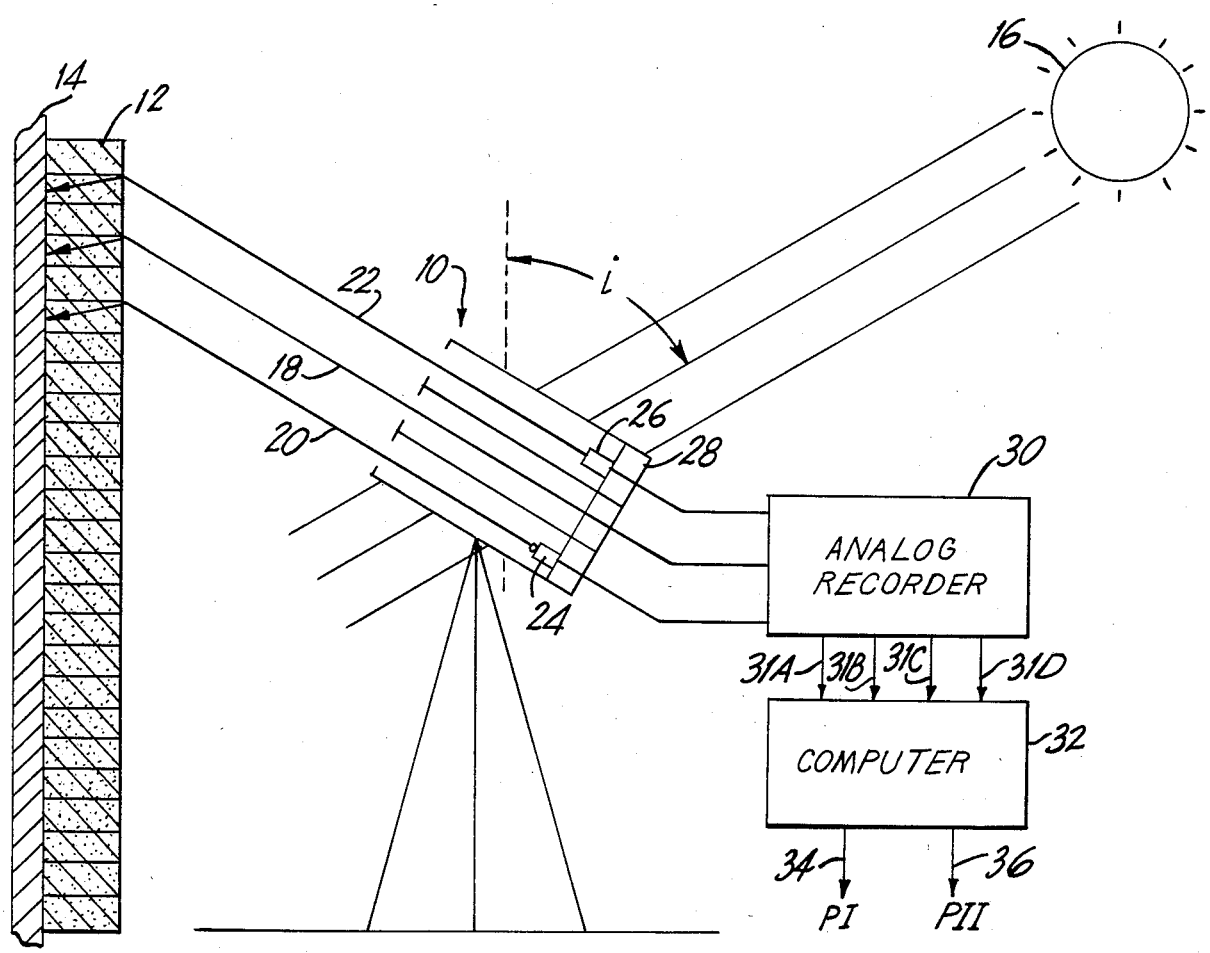
FIG. 2 is a schematic diagram of another embodiment of a polarimeter apparatus for carrying out the present invention for substantially vertical targets.

Referring to FIG. 2, the polarimeter 10 is shown in use for geological remote sensing of the nature of a substantially vertical earth surface composition. The polarimeter 10, again mounted on a rigidly positioned transit base, is aimed directly at the sun and elevation and azimuth angles are recorded. The polarimeter 10 is then aimed at the ground at the same azimuth angle increased by 180° and at an elevation angle equivalent to the formerly recorded elevation angle. Targets on an east surface need an afternoon sun and a downward traverse. Targets on a west surface need a morning sun and an upward traverse. Operation of the polarimeter 10, recorder 30 and computer 32 is then the same as described previously herein with respect to the embodiment of FIG. 1. If (PI$\lambda n$=PI$\lambda n+3$); and, if (PI$\lambda n+1$=PI$\lambda n+2$), the same target in a traverse is observed to display equal polarization intensities by conjugate pairs of spectra. If these conjugate pairs of spectra also display unequal magnitudes of polarization intensities respectively in which PI$\lambda n$/PI$\lambda n+3$ is greater than PI$\lambda n+1$/PI$\lambda n+2$, such targets are near vertical in orientation and such targets are homogeneous in substance. For correlation of such vertical targets with similar vertical targets, the Polarization Intensity Intensity Index of Vertical Targets ($PII_V$) =

$$\frac{(PI\lambda n + PI\lambda n + 3) - (PI\lambda n + 1 + PI\lambda n + 2)}{(PI\lambda n + PI\lambda n + 3) + (PI\lambda n + 1 + PI\lambda n + 2)}$$

If the vertical target is not homogeneous, PI$\lambda n$ through PI$\lambda n+3$ will all vary with respect to one another.

The accuracy of the photopolarimeter 10 is sensitive to changes in the light irradiation incident on its collecting lenses due to possible motion of the polarimeter 10. Consequently, the photopolarimeter 10 should be immobile and stationary although the photopolarimeter 10 may be allowed to move relative to the target surface such as in a satellite orbit about the earth.

The invention is not limited to the use of natural sunlight. Artificial illumination such as by linearly polarized light incident on the target surface may be employed.

The definition of surface does not preclude penetration into the reflecting material to some extent.

While various modifications and variations have been suggested in the course of the description, it should be pointed out that the invention is not limited in scope to the specific embodiments described or suggested. For example, radiations of different wavelengths such as cosmic rays, gamma rays, X-rays, ultra violet below 4000 Å, infra red greater than 7000 Å, Hertzian waves beyond $2.2 \times 10^4$ and the like may be employed.

In the consideration of the band selection for polarimetry measurement according to the present invention, the factors discussed hereinbelow should be considered. In a controlled and relatively stable system (as in a vacuum with standard temperature and pressure) attenuation of Irradiance (I) is a natural straight line function that generally increases with increasing wave lengths. By irradiance is meant the radiant power incident on a surface and by attenuation is meant the intensity loss of radiation according to Lambert's Law. There are some interruptions in the symmetry of the straight line function of Irradiance attenuation, especially at sea level, but less so outside of the earth's atmosphere. This lack of symmetry is small at 0.5–0.6 microns ($\lambda_n$) and at 0.6–0.7 microns ($\lambda_{n+1}$); large but narrow at 0.7–0.8 microns ($\lambda_{n+2}$); and large at 0.8–1.1 microns ($\lambda_{n+3}$).

The variances in symmetry are generally internal to applicant's four spectral bands. If such regularly decreasing irradiance, I, is impacted by any stress, the irradiance should change depending upon the pertinent vectors and the degrees of freedom in the system. If a stress, such as the Doppler Effect, were uniformly applied, its differential values would parallel the attenuation slope. Such a result would be achieved with a homogeneous target stressed under identical conditions. Departures from such parallelism would indicate heterogeneity. The intensity would be proportional to the calculus slope derivative of the spectra affected. PI can be considered as a concomitant of attenuation because, in general, the longer the wavelength, the greater the polarization. In brief, as natural attenuation takes place by wavelength, polarization increases or decreases as the wavelengths increase or decrease, respectively. Under homogeneous conditions, i.e., equal refractive indices and identical conditions, attenuation and polarization will be related and equal respectively for light reflected by Fresnel's Laws even when the refractive index is complex. This relationship will hold for all wave length segments whose natural and intrinsic attenuation by wave length is a straight line function. In this connection, the relative ease of reading of irradiance amplitudes in the visible portion of the electromagnetic spectrum offers an advantage. However, any other segments of the electromagnetic spectrum could be used under natural and/or suitable empirical conditions according to the method of this invention.

In the visible segment of the electromagnetic spectrum, up to about 2.5 micro-meters, the attenuation curves increase for clouds and moisture in the atmosphere. However, the slopes of these curves have a general parallelism which can be detected by suitable telemetry of the respective amplitudes of Irradiation Flux. Adverse stresses such as smog or pollution, if mutual to the optical elements of the system, need not interfere with the correlative values of the amplitudes directly recorded by wave lengths with good linearity. Light is either absorbed by particles suspended in the atmosphere such as dust, haze, smog, fog or rain and then is emitted in all directions (true scattering), or light is simply reflected by the surface of the particle. Scattering diverts some of the light from the target so that it does not enter the collector of the remote sensing means, or diverts light that is not part of the target being observed into the collector of the remote sensing means. The result in either case is a reduction in contrast. This contrast reduction, often specified numerically in terms of a modulation transfer function, is caused by scattering. Scattering may be countered by use of filters in the remote sensing means that tend to pass light that has not been scattered and to block light that has been scattered, or by using a remote sensing means that operates at the millimeter and centimeter wavelengths (microwaves) that can pass through fog and clouds with a minimum of attenuation.

Figure 3:
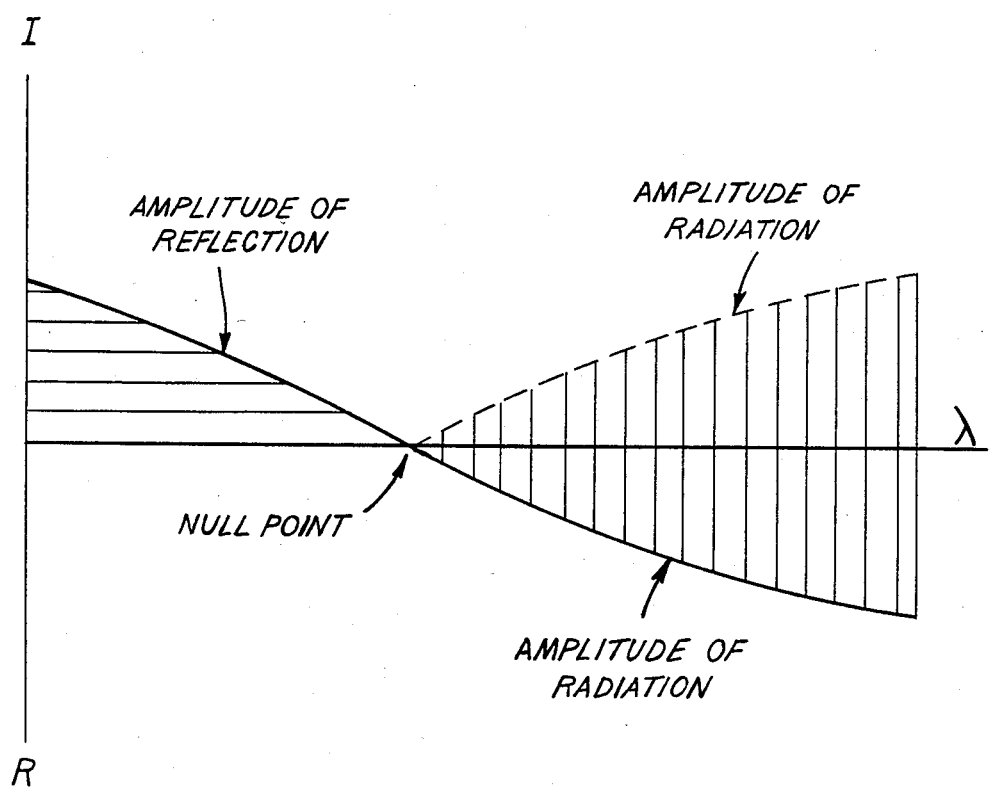
FIG. 3 is a graph schematically illustrating the relationship of reflection and radiation as a function of wave length to show the null point of amplitude.

It is recognized that when the spectra no longer reflect (spectra longer than 2.5 micro-meters) that the telemetry must measure radiation in lieu of reflection. (See FIG. 3.) It is believed that the radiation amplitudes increased linearly by increased wave lengths will exhibit phenomena similar to the reflective irradiance amplitudes. Combinations of simultaneous telemetry for reflective irradiance and radiation may be mutually advantageous for remote sensing because the null point is a common and natural index where reflectance ends and radiation begins. For example, two remote sensing means of this invention may be employed operating at different frequency bands to gather data about a target surface and then the separate results compared. Thus, both reflective and emissive spectra can be simultaneously measured by two separate remote sensing means to gather data in the full range of the electromagnetic spectrum.

As indicated previously herein, different wave length bands can be employed in conjunction with the remote sensing means according to this invention. The visible portion of the electromagnetic spectrum extends from 0.4 to 0.7 micrometers. The portion 0.3 to 15 micrometers is the optical wavelength portion. Wave lengths shorter than 0.4 micrometers lie in the ultra violet region. Above the visible spectrum lies the infrared region; 0.7 to about 3 micrometers is called the reflective infrared region; and the region from 3 to 15 micrometers is called the emissive or thermal infrared region. Instead of energy being reflected in this latter region, it is emitted due to thermal activity or heat.

The null point reflection and radiation is a natural index point (See FIG. 3) for remote sensing with multi-spectral telemetry of targets. On the earth's surface, it could be significant when plotted with the agonic lines. Composite reflection-radiation telemetry, which includes spectral bands at and beyond the null point in decreasing and increasing wavelengths respectively, and used by applicant's method, will not only improve remote sensing, but also will identify options for information extraction of data already archived by rotation of axes and other empirical devices or algorithms using computers.

The intrinsic amplitude of irradiance for each spectrum is a discrete value composed of an integration of a harmonic and stochastic process in which synchronous limits are used instead of fixed limits. It is apparent that spectra should be chosen in pairs such that the ratios of their intrinsic amplitudes of irradiance ($I\lambda_n$ through $I\lambda_{n+3}$) are proportional in pairs with equal slopes but with different magnitudes.

It should also be appreciated that the apparatus has been described in a relatively simple form and that more complex apparatus could be utilized to increase the efficiency, for example, by using multiple photopolarimeters and/or automatically rotating the photopolarimeters to the desired angles. It will be understood therefore that such refinements together with automatic recording equipment and other known techniques could be utilized to increase the speed and efficiency of the apparatus disclosed and are within the scope of the invention.

The following examples illustrate a preferred embodiment of the method of this invention.

EXAMPLE 1

Two obstacles have sidetracked polarimetry. Polarization is known to affect all light from its sources through its recording. For remote sensing, this raises the problem of negating the optical thickness between the light source and the target. This problem applies to passive application with the sun or to active application with a controlled light source. No polarimeter has been developed for broad picture imaging. This example illustrates that digital interference spectroscopy of precisely registered polarization data of point-to-point traverses on well-known ground surfaces can be manipulated in computers to enhance discrimination or signature differences. Also, it illustrates that the traverses can be spaced to synthesize a mosaic or aerial coverage for targets of interest and that the optical thickness between the target and the polarimeter can be evaluated by comparing close, intermediate and long-range viewing of identical targets with temporal studies.

A polarimeter, the "visible Light Polarimeter Lab. Type SO46" (commercially available from General Electric Company Space Division, P.0. Box 8555, Philadelphia, Pa. 19101) was fitted with and calibrated to record polarization by Stokes parameters in four wave bands: $\lambda_n = 0.5$–$0.6$ microns; $\lambda_{n+1} = 0.6$–$0.7$ microns; $\lambda_{n+2} = 0.7$–$0.8$ microns; and $\lambda_{n+3} = 0.8$–$1.1$ microns. The polarimeter was used in conjunction with two interchangeable, portable surveyor's tripods with cross-leveling. The polarimeter was mounted on the other tripod during traverses of targets. The two tripods provided precise registration of the polarimeter during traverses was made at about eye level. The polarimeter was made portable by employing two interchangeable portable power packs with a five hour capacity and fitted for recharge and connections on standard 110 V-60 cycle service. The engineering transit style configuration of tripod was mounted with precision controls for orientation, azimuth and elevation. The surveying configuration was needed to track the sun in elevation and azimuth for the purpose of exploiting passively the solar flux and documenting the look angle for each target.

The field of view of the polarimeter is dependent on its distance from a target. At twenty feet distance, its field of view subtends a circle of one foot diameter. At ten feet, its field subtends distance, a circle of one-half foot diameter. At thirty feet, its field subtends a circle of one and one-half foot diameter. No picture image is formed within the target circle as in photography. The data that are recorded are the polarization intensities of the target surface. Since polarization has an intrinsic resolving power much more delicate than available in the usual lens systems, the correlation of surface truth with these data provides an improved method of remote identification of targets.

The polarimeter itself had a cylindrical case about 5 inches in diameter and 16 inches in length. The case had 5 barrels drilled coaxially with its longitudinal axis. Two of these barrels were fitted with dessicants to eliminate the formation of moisture on the optical elements fitted into the remaining three barrels. Two polarizing prisms specifically cut from calcite crystals were mounted in adjacent barrels, with their directions set perpendicular to each other, along a common fixed plane. The two polarizing prisms acted as filters to pass only the vertical and horizontal components of plane polarized light reflected by each target surface. These barrels were labeled B and D. Between these barrels with the prisms and in the same common plane (perpendicular to the longitudinal axis of the case) were apertures which pass light flux being reflected by the target surface. This barrel was labeled ½ (I).

To the rear of the fixed B-D-I plane, there was fitted a parallel rotating plane with four spectral filters on a common arc in the four wave bands previously described herein. These filters passed the vertical and horizontal components of polarized reflectance from the target simultaneously for their respective wave bands concurrently with the unfiltered flow of the light flux reflected from the target. The timing was geared to a Geneva Movement so that one complete pulse of all four bands was cycled in 1.3 seconds. This provided a code print-out of Q,U and ½ (I) for each of the four spectral bands, $\lambda_n$ through $\lambda_{n+3}$, respectively. Q, U and I are, of course, the Stokes Parameters for polarized light. They were converted to polarization intensity (PI) by solving the following quadratic equation for each of the four spectral bands:

$$100\, PI = 100 \sqrt{\frac{Q^2 + U^2}{I^2}}$$

The polarimeter was fitted to a biaxial yoke with a transit style mounting as previously indicated herein to facilitate precise orientation and registration of traverses by latitude and longitude. In addition, the case of the polarimeter was fitted with a gun sight telescope for manual tracking of the sun or other targets. The polarimeter was also linked by a cable to a central control panel and electronics package powered by a portable battery unit with an AC inverter and a constant voltage device. The control panel was linked by cable to a recorder that printed out the Stokes Parameters cyclically in twelve coded line pulses by band sequence, $\lambda_n$ through $\lambda_{n+3}$.

A target surface situated at Boling Dome, Newgulf, Tex. was selected for a traverse with the polarimeter. The mounting tripod was surveyed in at the desired centerpoint of the traverse using map coordinates of this area and a compass. The polarimeter, in its biaxial yoke, was set on the tripod so that alignment pins on the yoke mated with holes on the tripod head. A screw clamp was used to lock the yoke to the tripod. Scales on the horizontal and vertical axes of the yoke were used to record angular positions of the polarimeter. A gun-sight telescope, as previously mentioned, was fitted to the polarimeter to facilitate accurate aim at targets. Jack and plug fittings were employed to ensure proper linkage of the power unit, control panel, recorder and polarimeter.

The movement of the sun was manually tracked with the telescope. Measurements were taken and recorded at ½ hour intervals. A few seconds prior to recording, the polarimeter was lowered below a horizontal orientation to intercept the surface target at an angle equal to the elevation angle of the sun. Print outs were made using the polarimeter apparatus for about 6 seconds so as to obtain 4 complete sets of data.

The polarimeter was set up on the top of a man-made vat of native sulfur stock-piled fifty feet above the ground by the Frasch process of mining. Readings of a selected target surface of the vat were taken according to the procedure outlined hereinabove. The two wave bands λn and λn+1 had equal polarization intensities while the two wave bands λn+2 and λn+3 also had equal polarization intensities but of a different magnitude than the pair, λn and λn+1.

The polarimeter was displaced 150 feet due west of its original location on the vat to test afternoon data on the vat-ground interface. Data readings, using the procedure outlined hereinabove, when the polarimeter was aimed at this interface, indicated the interface was heterogeneous as expected since all four spectral bands provided unequal readings. However, as the polarimeter was aimed at target surfaces more distant from the vat, the conjugate pair phenomena reappeared indicating the homogeneity of the target surface. An example of data indicating sulfur vat surface homogenity is set forth in Table I hereinbelow:

ture was substantially identical to that of the PII reading taken for the same cow pasture at a different distance therefrom in example 1.

When readings were taken using as the target surface a road surface metalled with pebbles in a tarlike matrix, four unequal polarization intensities were measured, indicating a heterogeneous target surface.

EXAMPLE 3

Using the procedure described in Example 1, a stone quarry situated near Centreville Va. was identified according to applicant's method. The east and west walls of the stone quarry had near-vertical faces of exposed rock. With the afternoon sun, the instrument was surveyed in near the east quarry wall. With a morning sun, the instrument was surveyed in near the west quarry wall. The sun was then tracked manually with the aid of

TABLE I

| | STOKES PARAMETERS | | | | | | | | | | | | | |
|---|---|---|---|---|---|---|---|---|---|---|---|---|---|---|
| | Q | | | | | | | | U | | | | | |
| | DATA POSITIONS | | | | | | | | | | | | | |
| SPECTRA | 002 | 003 | 004 | 005 | 006 | 007 | 008 | 011 | 012 | 013 | 014 | 015 | 016 | 017 |
| =0.5μ to 0.6μ | 0 | 0 | . | 1 | 2 | 9 | 0 | 0 | 0 | . | 0 | 7 | 8 | 6 |
| =0.6μ to 0.7μ | 0 | 0 | . | 0 | 6 | 8 | 5 | 0 | 0 | . | 0 | 6 | 4 | 7 |
| =0.7μ to 0.8μ | 0 | 0 | . | 0 | 1 | 2 | 7 | 0 | 0 | . | 0 | 9 | 8 | 0 |
| =0.8μ to 1.1μ | 0 | 0 | . | 2 | 0 | 1 | 0 | 0 | 0 | . | 1 | 5 | 3 | 0 |

| | STOKES PARAMETERS ½(I) DATA POSITIONS | | | | | | | Polarization Intensity times 100 |
|---|---|---|---|---|---|---|---|---|
| SPECTRA | 021 | 022 | 023 | 024 | 025 | 026 | 027 | |
| =0.5μ to 0.6μ | 0 | 1 | . | 6 | 1 | 0 | 0 | 5.0 |
| =0.6μ to 0.7μ | 0 | 0 | . | 9 | 2 | 1 | 0 | 5.0 |
| =0.7μ to 0.8μ | 0 | 2 | . | 1 | 2 | 0 | 0 | 2.0 |
| =0.8μ to 1.1μ | 0 | 3 | . | 2 | 5 | 0 | 0 | 2.0 |

The polarimeter was displaced 20 feet due east of its original location on top of the vat. Readings were taken for the following target surfaces: an adjacent cow pasture, the sulfur vat, a sulfur surface about 55 feet below the polarimeter on the vat and the ground-vat interface. The conjugate pair phenomena was observed from the first three target surfaces but not for the interface, thus revealing the homogenity of the target surfaces by remote sensing means. Moreover, the PII of the cow pasture was different from the PII of the sulfur surface and the sulfur vat targets each had substantially identical PII values.

EXAMPLE 2

The procedure of Example 1 was repeated except that the polarimeter was set up on a platform 24 feet above the ground on the top of an oil storage tank in a pasture. Again when readings were taken using the polarimeter on a target consisting of the pasture, the conjugate pair of wave bands phenomena was indicated. Also, the readings of the PII for the target pasthe telescope. After ¼ hour intervals, without changing the tracking elevation, the polarimeter was rotated on its vertical axis in aximuth to intersect the closer quarry wall from which it received solar flux reflected from the quarry wall at about the same angle as the incident sunlight.

The track of the polarimeter readings was vertically downward on the east wall and vertically upward on the west wall. A pattern of percent polarization intensity evolved in conjugate pairs of wave lengths for homogeneous target surfaces. However, it differed from patterns for the generally horizontal target surfaces with $\lambda_n$ and $\lambda_{n+3}$ pairing and $\lambda_{n+1}$ and $\lambda_{n+2}$ pairing. Since the more horizontal surfaces had $\lambda_n$ and $\lambda_{n+1}$ pairing and $\lambda_{n+2}$ and $\lambda_{n+3}$ pairing as conjugate pairs, the regrouping was attributed to the vector translational speed of the sun source in a vertical plane versus vector translational speed of the sun-source in a horizontal plane. An example of data gathered in this experiment during the traverse of the vertical west wall of the quarry is reproduced below in Table II:

TABLE II

| | STOKES PARAMETERS | | | | | | | | | | | | | |
|---|---|---|---|---|---|---|---|---|---|---|---|---|---|---|
| | Q | | | | | | | | U | | | | | |
| | DATA POSITIONS | | | | | | | | | | | | | |
| SPECTRA | 002 | 003 | 004 | 005 | 006 | 007 | 008 | 011 | 012 | 013 | 014 | 015 | 016 | 017 |
| =0.5μ to 0.6μ | 0 | 0 | . | 0 | 9 | 5 | 5 | 0 | 0 | . | 0 | 0 | 4 | 9 |
| =0.6μ to 0.7μ | 0 | 0 | . | 0 | 4 | 5 | 7 | 0 | 0 | . | 0 | 0 | 0 | 6 |
| =0.7μ to 0.8μ | 0 | 0 | . | 0 | 8 | 9 | 0 | 0 | 0 | . | 0 | 0 | 5 | 9 |
| =0.8μ to 1.1μ | 0 | 0 | . | 1 | 4 | 9 | 0 | 0 | 0 | . | 0 | 0 | 4 | 9 |

| STOKES PARAMETERS ½(I) | Polarization Intensity |

TABLE II-continued

| SPECTRA | DATA POSITIONS | | | | | | | times 100 |
|---|---|---|---|---|---|---|---|---|
| | 021 | 022 | 023 | 024 | 025 | 026 | 027 | |
| =0.5μ to 0.6μ | 0 | 0 | . | 5 | 6 | 5 | 0 | 8.0 |
| =0.6μ to 0.7μ | 0 | 0 | . | 3 | 0 | 6 | 0 | 7.0 |
| =0.7μ to 0.8μ | 0 | 0 | . | 6 | 8 | 6 | 0 | 7.0 |
| =0.8μ to 1.1μ | 0 | 0 | . | 9 | 0 | 3 | 0 | 8.0 |

The significance of this grouping of conjugate pairs differing for vertical surfaces makes possible the exploration of wells and canyons by polarimetry with controlled illumination sources. Also, controlled light sources can be tailored to range and navigate on selected signature isopleths of surfaces for mineral exploration and the like.

In addition to all the previously suggested modifications and variations, other variations will be apparent to those of ordinary skill in the art and it is accordingly desired that the scope of the invention not be limited to those embodiments disclosed nor to the several variations and modifications suggested but that the scope of the invention be limited only by the appended claims.

What is claimed is:

1. A non-contact method for remote sensing of the homogeneity of a substantially horizontal unidentified target surface comprising:

electro-optically detecting a train of optical waves reflected from said target surface with a photopolarimeter;

calculating the polarization intensities (PI's) of said detected optical wavelengths in four preselected spectral wave bands, $\lambda_n$ through $\lambda_{n+3}$, wherein $0.5 < \lambda_n \leq 0.6$ micrometers, $0.6 < \lambda_{n+1} \leq 0.7$ micrometers, $0.7 < \lambda_{n+2} \leq 0.8$ micrometers and $0.8 < \lambda_{n+3} \leq 1.1$ micrometers;

calculating a polarization intensity index (PII) for said target surface by ratioing the difference between $(PI\lambda n + PI\lambda n + 1)$ and $(PI\lambda n + 2 + PI\lambda n + 3)$ with the sum of $(PI\lambda n + PI\lambda n + 1) + (PI\lambda n + 2 + PI\lambda n + 3)$, provided that the PI of the four wave bands define two conjugate pairs PIλn with PIλn+1 and PIλn+2 with PIλn+3 each conjugate pair having the same PI, and the conjugate pairs PIλn with PIλn+1 and PIλn+2 with PIλn+3 being different from one another; and comparing the calculated PII for said target surface with PII values for predetermined target surfaces to identify said unidentified target surface.

2. A non-contact method for remote sensing of the homogeneity of a substantially vertical unidentified target surface comprising:

electro-optically detecting a train of optical waves reflected from said target surface with a photopolarimeter;

calculating the polarization intensities (PI's) of said detected optical wavelengths in four preselected spectral wave bands, $\lambda_n$ through $\lambda_{n+3}$, wherein $0.5 < \lambda_n \leq 0.6$ micrometers, $0.6 < \lambda_{n+1} \leq 0.7$ micrometers, $0.7 < \lambda_{n+2} \leq 0.8$ micrometers and $0.8 < \lambda_{n+3} \leq 1.1$ micrometers;

calculating a polarization intensity index (PII) for said target surface by ratioing the difference between $(PI\lambda n + PI\lambda n + 3)$ and $(PI\lambda n + 1 + PI\lambda n + 2)$ with the sum of $(PI\lambda n + PI\lambda n + 3) + (PI\lambda n + 1 + PI\lambda n + 2)$ provided that the PI of the four wave bands define two conjugate pairs PIλn with PIλn+3 and PIλn+1 with PIλn+2 each conjugate pair having the same PI, and the conjugate pairs PIλn with PIλn+3 and PIλn+1 with PIλn+2 being different from one another; and comparing the calculated PII for said target surface with PII values for predetermined target surfaces to identify said unidentified target surface.

3. A non-contact method for identifying a substantially horizontal unidentified target surface which comprises the steps of:

electro-optically receiving the polarized components of a train of electro-magnetic radiation reflected from said target surface;

electro-optically generating four first data signals representative of four first values corresponding to the Stokes parameter Q, for four respective, preselected wave bands of said reflected radiation;

electro-optically generating four second data signals representative of four second values corresponding to the Stokes parameter U, for said four respective, preselected wave bands of said reflected radiation;

electro-optically generating four third data signals representative of four third values corresponding to the Stokes parameter $\frac{1}{2}(I)$ for said four respective, preselected wave bands of reflected radiation;

electro-optically operating on the first, second, and third data signals for each respective wave band to compute a fourth, fifth, sixth and seventh data signal representative of the polarization intensity for said four respective wave bands;

electro-optically operating on said fifth and said sixth data signals to compute a difference between them;

electro-optically operating on said fifth and sixth signals to compute their sum;

electro-optically computing a ratio of said difference to said sum which ratio represents the polarization intensity index of said unidentified target surface;

comparing said polarization intensity index of said target surface with the polarization intensity indexes of previously determined surfaces to identify said target surface.

4. A non-contact method for identifying a substantially vertical unidentified target surface which comprises the steps of:

electro-optically receiving the polarized componenets of a train of electro-magnetic radiation reflected from said target surface;

electro-optically generating four first data signals representative of four first values corresponding to the Stokes parameter Q, for four respective preselected wave bands of said reflected radiation;

electro-optically generating four second data signals representative of four second values corresponding to the Stokes parameter U, for said four respective preselected wave bands of said reflected radiation;

electro-optically generating four third data signals representative of four third values corresponding to the Stokes parameter $\frac{1}{2}(I)$ for said four respective, preselected wave bands of reflected radiation;

electro-optically operating on the first, second and third data signals for each respective wave band to compute a fourth, fifth, sixth and seventh data signal representative of the polarization intensity for said four respective wave bands;

electro-optically operating on said sixth and seventh data signals to compute a difference between them and their sum;

electro-optically computing a ratio of said difference to said sum which ratio represents the polarization intensity index of said unidentified target surface;

comparing said polarization intensity index of said target surface with the polarization intensity indexes of previously determined surfaces to identify said target surface.

5. A method as defined in claims 1,2,3, or 4 wherein said radiation comprises sunlight.

* * * * *